US010215675B2

(12) United States Patent
Khosla et al.

(10) Patent No.: US 10,215,675 B2
(45) Date of Patent: Feb. 26, 2019

(54) UNIVERSAL MATERIAL TESTER WITH QUICK-RELEASE TEST PROBE AND WITH REDUCED CROSS-TALK BETWEEN THE SENSORS

(71) Applicant: Rtec-Instruments, Inc., San Jose, CA (US)

(72) Inventors: Vishal Khosla, San Jose, CA (US); Nick Doe, San Jose, CA (US); Jun Xiao, San Jose, CA (US); Ming Chan, San Jose, CA (US); Gautam Char, San Jose, CA (US)

( * ) Notice: Subject to any disclaimer, the term of this patent is extended or adjusted under 35 U.S.C. 154(b) by 223 days.

(21) Appl. No.: 15/256,668

(22) Filed: Sep. 5, 2016

(65) Prior Publication Data

US 2018/0067031 A1    Mar. 8, 2018

(51) Int. Cl.
*G01N 3/56* (2006.01)
*G01N 19/02* (2006.01)
*G01N 3/40* (2006.01)

(52) U.S. Cl.
CPC .............. *G01N 3/56* (2013.01); *G01N 3/40* (2013.01); *G01N 19/02* (2013.01); *G01N 2203/0206* (2013.01)

(58) Field of Classification Search
CPC .. G01N 3/46; G01N 3/50; G01N 3/56; G01N 19/02; G01N 2203/0206; G01D 11/245
USPC .................................................. 73/1.89, 7, 9
See application file for complete search history.

(56) References Cited

U.S. PATENT DOCUMENTS

| 4,785,673 A * | 11/1988 | Aumard ............... G01G 3/1412 177/211 |
| 6,324,918 B1 | 12/2001 | Gitis et al. |
| 6,363,798 B1 * | 4/2002 | Gitis et al. ............ G01L 1/2243 73/862.381 |
| 6,418,776 B1 * | 7/2002 | Gitis et al. ............... G01N 3/56 73/10 |
| 7,958,790 B2 * | 6/2011 | Gleghorn et al. ...... G01L 5/161 73/10 |
| 2015/0075250 A1 | 3/2015 | Kosa et al. |
| 2016/0290797 A1 * | 10/2016 | Bos et al. .............. G01B 21/04 |

FOREIGN PATENT DOCUMENTS

WO    WO 2010040326 A1 *  4/2010    ............. G01N 3/062

OTHER PUBLICATIONS

Bibliographic Data containing abstract for WO 2010040326 A1, Date: Apr. 15, 2010, Publisher: Espacenet, pp. 2.*

\* cited by examiner

*Primary Examiner* — Lisa M Caputo
*Assistant Examiner* — Roger G Hernandez-Prewitt

(57) ABSTRACT

The sensor unit of the material tester consists of a pressure-sensor unit that measures a vertical force applied to the test probe during movement of the test probe relative to the test specimen and a horizontal force sensor unit for measuring the horizontally directed friction force. The horizontal force sensor unit is made in the form of a flexible parallelogram consisting of two sensor-holding plates interconnected through flexible beams, wherein one end of the first beam is attached to the upper sensor-holding plate and the opposite end to the lower sensor-holding plate, while one end of the second beam is attached to the lower sensor-holding plate and the other to the upper one. The beams are installed with gaps relative to both plates. The quick-release test probe incorporates a soft-touch feature.

17 Claims, 7 Drawing Sheets

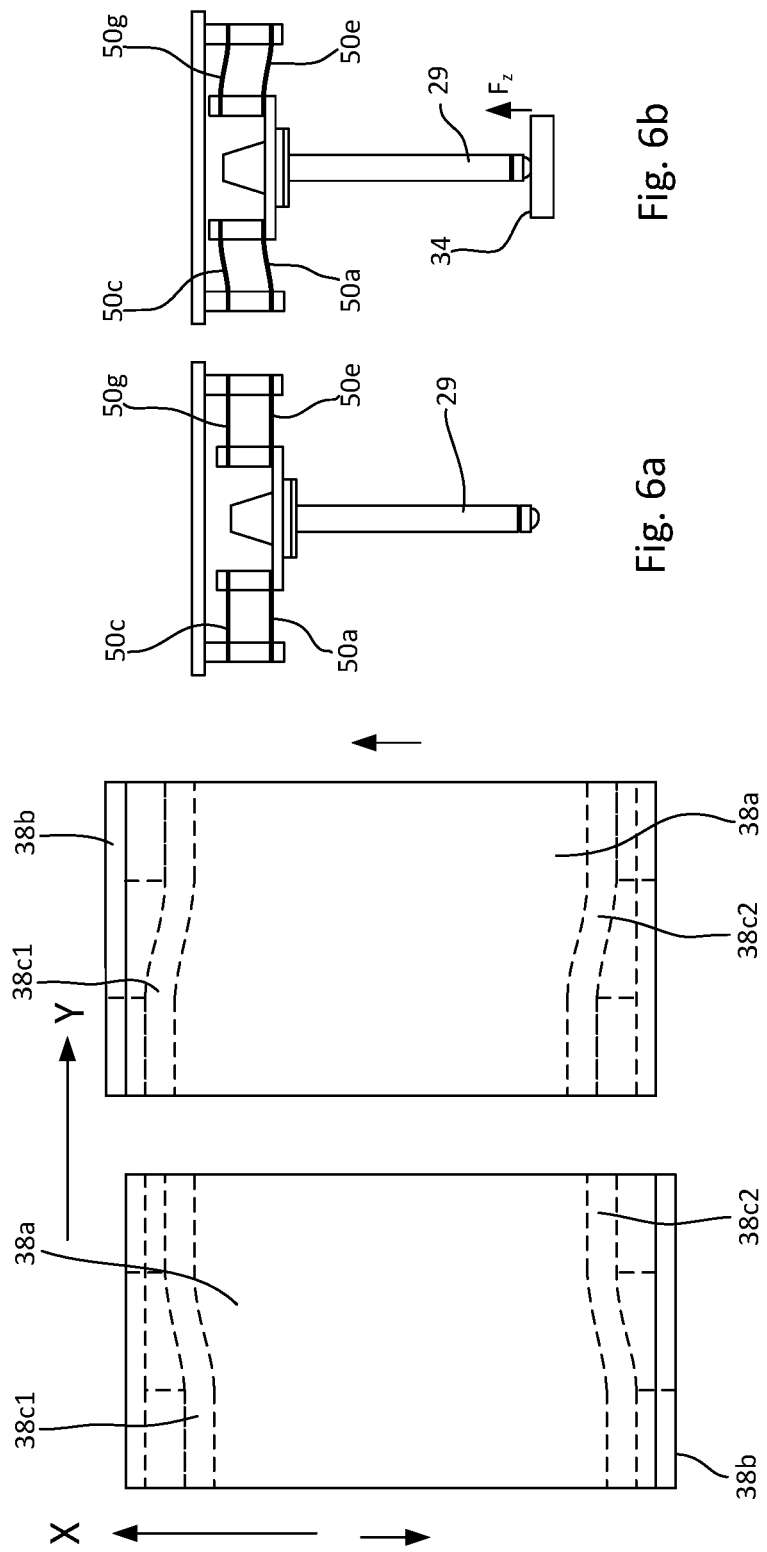

UNIVERSAL MATERIAL TESTER WITH QUICK-RELEASE TEST PROBE AND WITH REDUCED CROSS-TALK BETWEEN THE SENSORS

BACKGROUND OF THE INVENTION

Field of the Invention

The present invention relates to the field of material property testing, in particular to a tester for measuring characteristics of materials such as hardness, resistance to wear, friction forces developed during the test, etc. The invention also relates to a tester of the aforementioned type with a quick-release test probe that incorporates a soft-touch feature.

Description of the Related Art

There exists a plurality of material testers for measuring various properties of the materials, such as hardness, friction forces that develop during mutual friction of moveable parts, resistance to wear, etc.

Irrespective of whether testers are intended for measuring mechanical properties such as hardness or for friction properties, they have to measure forces, and this requires the use of different types of strain-gauges and other devices for force measuring.

For example, U.S. Pat. No. 6,324,918 issued in 2001 to N. Gitis, at all, describes a bidirectional force sensor for measuring two forces applied in two non-parallel directions on a friction tester. The tester has an upper rod-like probe made from the material being tested and a lower disk-like test material specimen, which performs rotary motions relative to the rod-like specimen in contact with the latter.

This sensor itself is made in the form of flexible dumbbell-shaped beam of a rectangular cross section with rigid solid end blocks at both ends for securing the sensor in the tester. The beam is provided with two through slots symmetrically cut in mutually perpendicular directions so that they are partially intersected within a body of the beam. Each slot has notches at its opposite ends which are wider than the slots so that the distance from the inner wall of the notch to the outer side surface of the beam is shorter than the distance to this surface from the inner wall of the slot. Mutually perpendicular surfaces at the ends of the beam support strain gauges. The beams are flexible in the direction of the force being measured but are rigid in the perpendicular direction. Under effect of the loading force applied to the lower material specimen from the probe and the friction force developed in the contact between the probe and the specimen, the flexible beam acts as a pair of overlapped and mutually perpendicular parallelograms.

A problem associated with the above-described tester is that the upper probe has a leverage with respect to the point of attachment of the lower specimen, i.e., with respect to its center. As a result, the loading force applied to the lower specimen via the upper probe, as well as the reaction force applied to the probe from the lower specimen, create an unbalanced momentum and deformations in the force measurement system. This leads to a distortion of measurements produced by the sensors and thus complicates interpretation of the measurement results.

U.S. Pat. No. 6,363,798 issued in 2002 to N. Gitis, at al., describes another device for measuring a loading force, which can be used for measuring, e.g., hardness and a friction force in a tribology tests. The device consists of two deformation-sensitive sensors for simultaneous equal deformation in two opposite directions for eliminating misbalance created in the measurement system when a single sensor is used. Each sensor is a deformable beam having through longitudinal slots extending in different and non-parallel directions and overlapped within the body of the beam. The sensor deforms in one direction under the effect of a loading force measured by two pairs of strain gauges located on opposite sides of the beam near one end of the beam and in another direction under the effect of a friction force measured by another two pairs of strain gauges located on opposite sides of the beam near the other end of the beam. Two sensors are sandwiched between two plates in a diagonally symmetrical positions so as to transmit forces between both plates and at the same time to ensure limited freedom of movement between both plates to allow deformations caused by the applied forces. One plate may be attached to the loading unit of the tester and another plate may support an upper sample for engagement with the lower sample of the tester.

Since this friction force is applied to a sample mounted in a long holder, this creates a significant torsional moment in the force sensor directly proportional to the magnitude of the friction force and to the length of the holder.

Furthermore, because of transverse through cuts, the flexible beams have reduced cross-sections and this, in turn, reduces the torsional stiffness of the force sensor and thus leads to significant torsional deformations of the force sensor sensitive elements. These torsional deformations could be a source of additional errors in force measurement.

SUMMARY OF THE INVENTION

The present invention provides a reliable and cost-effective universal material tester for measuring hardness, wear and friction properties, etc., with reduced cross-talk between the sensors. This is achieved by providing the tester with a sensor unit having the structure and the geometry of its parts that completely isolate deformations of the parts in the Z-axis direction from the deformations of the parts in the X-axis direction. As a result, it is possible to exclude cross-talks between the sensors acting in the Z-axis direction and the sensors acting in the X-axis direction. The invention also relates to a tester of the aforementioned type with a quick-release test probe that incorporates a soft-touch feature due to the provision of leaf springs in a resilient probe holder and that allows quick replacement of the test probe and probe tip for switching, e.g., from hardness test to tribology tests, or the like.

BRIEF DESCRIPTION OF THE DRAWINGS

FIGS. 5(a) and 5(b) are top views of the resilient probe holder of FIG. 3 illustrating deformations of the holder in the X-axis direction under the effect of a friction force applied to the probe from the test specimen.

FIGS. 6(a) and 6(b) are side views of the resilient probe holder of FIG. 3 illustrating deformations of the holder in the Z-axis direction under the effect of a vertical load applied to the probe from the test specimen.

DETAILED DESCRIPTION

Figure 1:
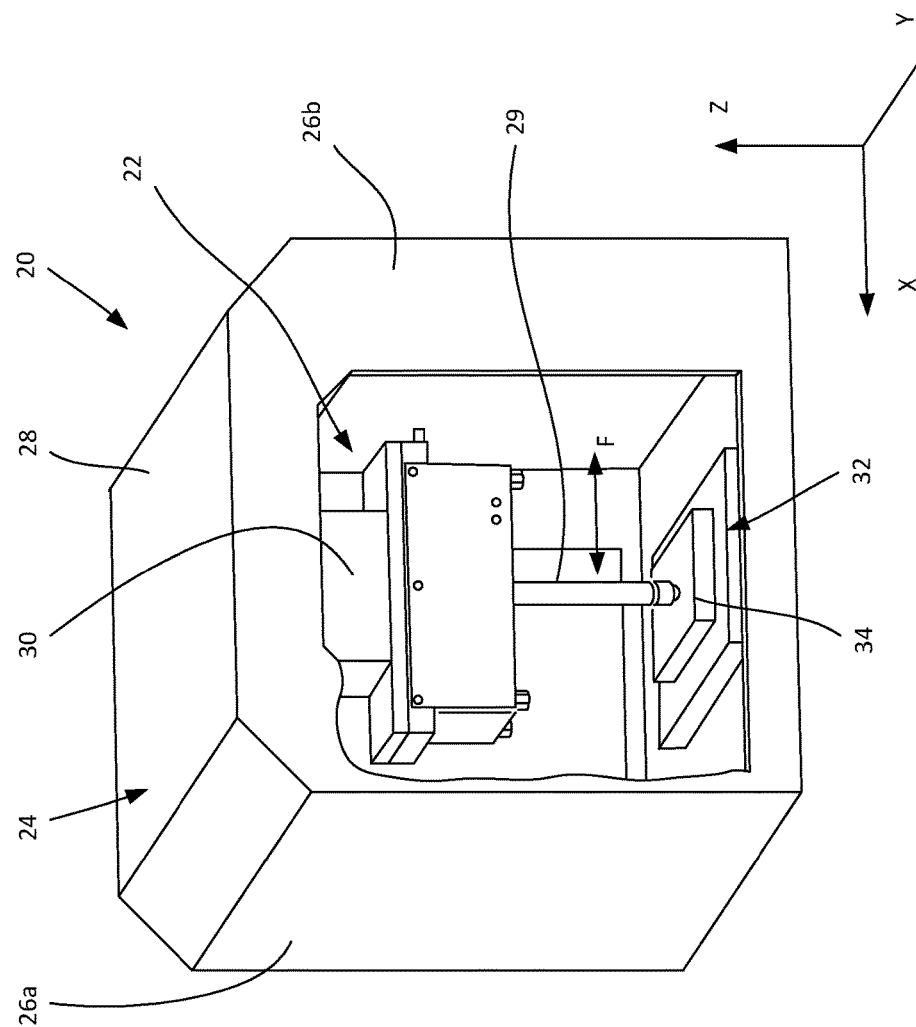
FIG. 1 is a general three-dimensional view of the universal wear and friction tester of the invention.

A general three-dimensional view of the universal material tester of the invention (hereinafter referred to merely as a tester), which in its entirety is designated by reference numeral 20, is shown in FIG. 1. In fact, the general structure of the tester of the invention with regard to the housing, specimen movement mechanisms, etc. is the same as one shown in our pending U.S. patent application Ser. No. 15/214,623 filed on Jul. 20, 2016 by the same applicants. In other words, similar to the tester of the invention disclosed in the aforementioned patent application, along with tribology properties, the tester of the present invention may measure such characteristics of the material as hardness, etc.

The main difference is in the structure of a sensor unit 22 secured in the tester housing 24 and in a device for connection and disconnection of the test probe. More specifically, the housing 24 of the tester 20 has columns 26a and 26b which extend vertically and are interconnected by a horizontal crossbar 28. The crossbar 28 is provided with an attachment unit 30 for attaching and securing a quick-release test probe 29 (hereinafter referred to simply as a "test probe 29") of the sensor unit 22.

The tester 20 is also provided with a moveable stage 32 that has drive mechanisms (not shown) in the direction of three mutually perpendicular axis X, Y, Z as shown in FIG. 1, where the movements in the X and Y axes are used for measuring tribology properties, and the movement in the Z-axis direction is used for measuring hardness and the vertical loading force. An example of such drive mechanisms is shown and described in aforementioned pending patent application of the same applicants.

Reference numeral 34 designates a specimen which is secured to the upper surface of the moveable stage 32 and which is brought into contact with the test probe 29 secured above the moveable stage 32 in the attachment unit 30. The upper part of the tester 20, and hence the probe 29, is stationary, and contact of the test specimen 34 with the test probe 29 is provided by moving the moveable stage 32 in the Z-axis direction. The probe 29 may be made from a material the same as or different from the material of the test specimen 34, or may have a replaceable tip for measuring hardness.

Figure 2:
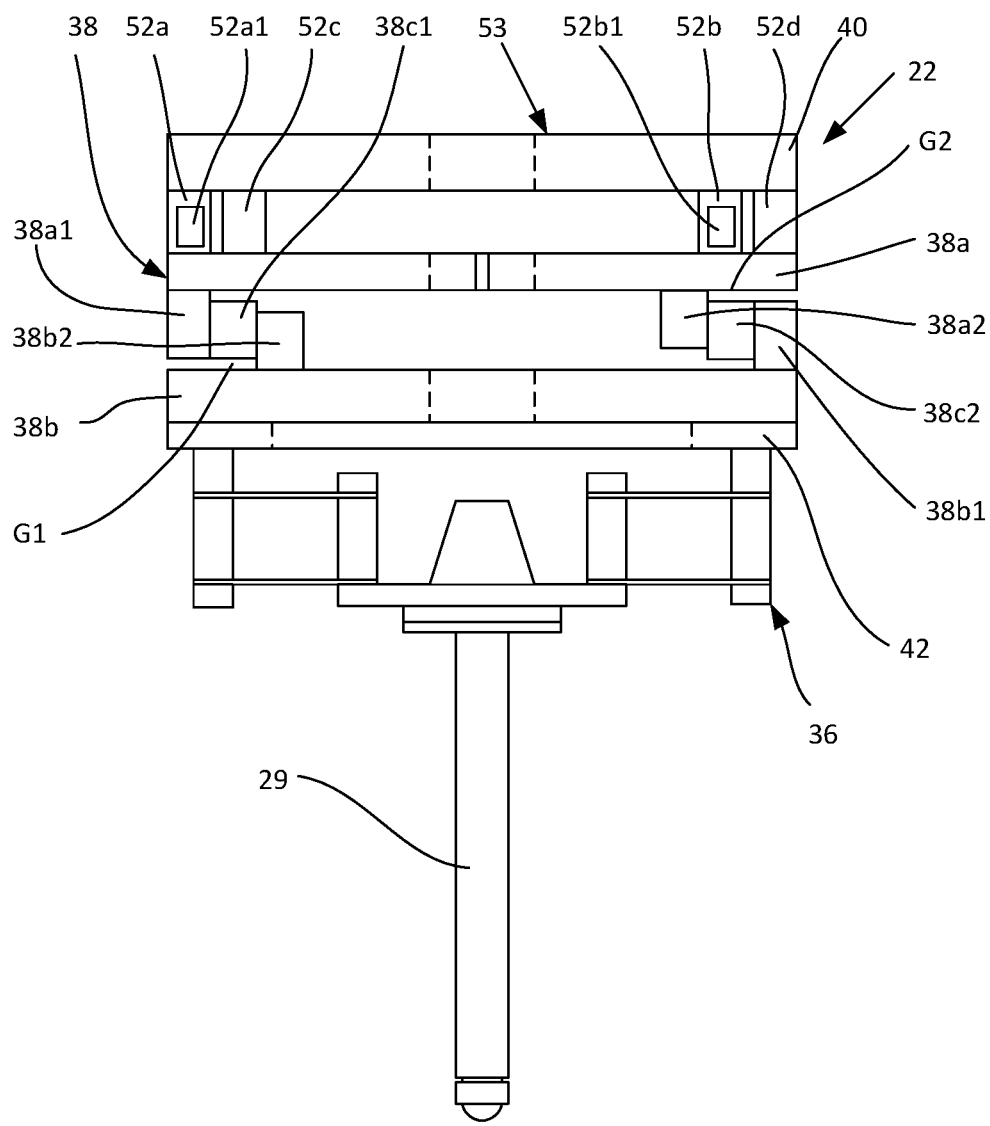
FIG. 2 is a side view of the sensor unit of the invention in an assembled state.
Figure 3:
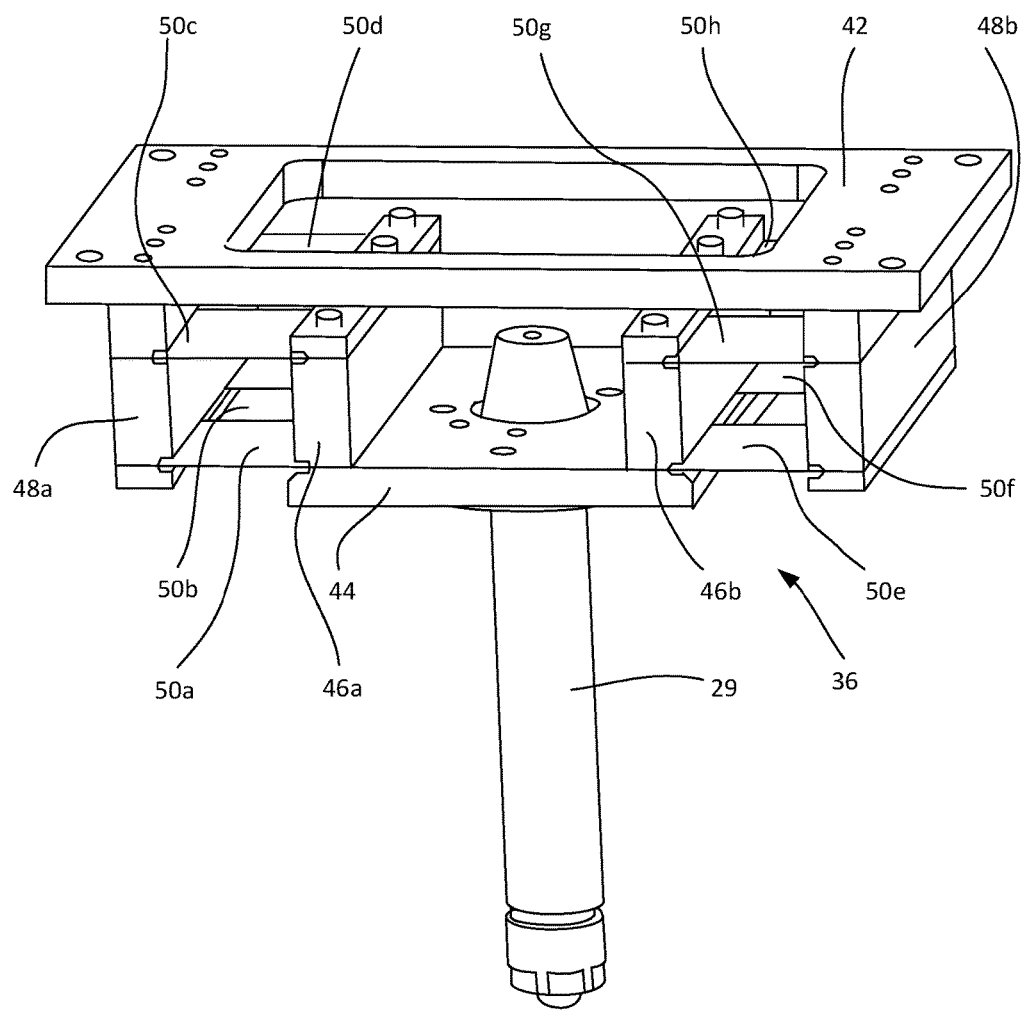
FIG. 3 is a three-dimensional view of a resilient probe holder of the invention with a test probe attached to the holder.
Figure 4:
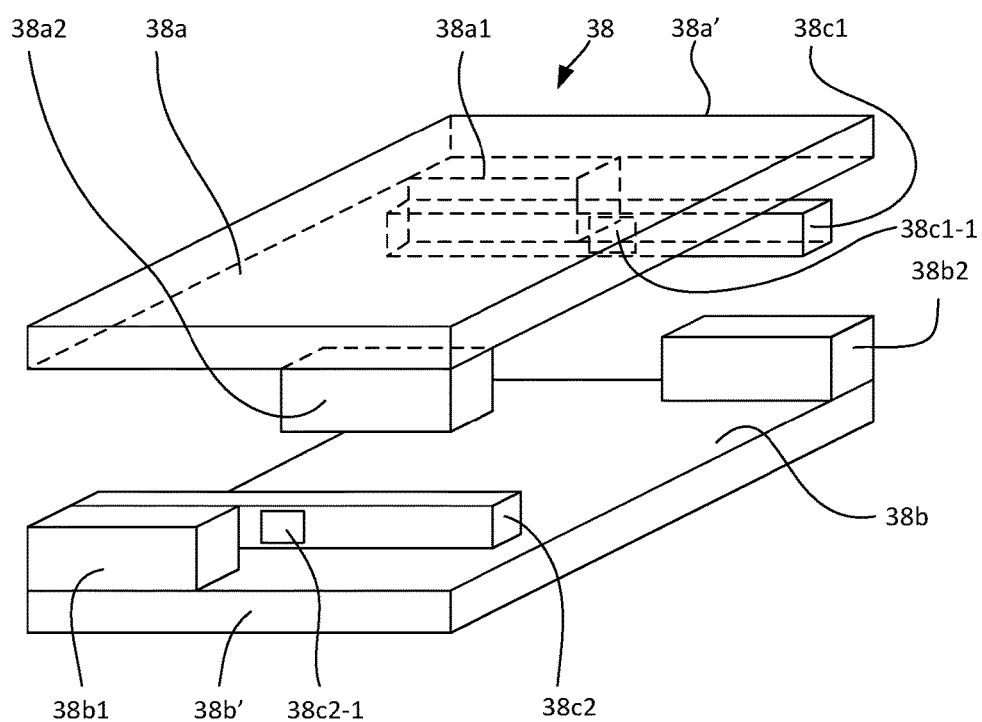
FIG. 4 is an exploded three-dimensional view of a sensor-holding sub-unit that constitutes a part of the sensor unit.

Having described the structure of the housing and movements pertaining to the tester 20 in general, let us consider now the main unique unit of the present invention, i.e., the sensor unit 22, which is shown in FIGS. 2, 3, and 4, wherein FIG. 2 is a side view of the sensor unit 22, FIG. 3 is a three-dimensional view of a resilient probe holder 36 with the test probe 29, and FIG. 4 is an exploded three-dimensional view of a horizontal-axis sensor-holding sub-unit 38, herein after referred to as a X-axis sensor-holding sub-unit 38 of the sensor unit 22.

As shown in FIG. 2, the upper side of the X-axis sensor-holding sub-unit 38 is attached to an adapter plate 40 used for securing the sensor unit 22 to the attachment unit 30 (FIG. 1), and the lower side of the X-axis sensor-holding sub-unit 38 holds the resilient probe holder 36.

The resilient probe holder 36 consists of a probe-holder upper plate 42 and a probe-holder lower plate 44 having dimensions smaller than the probe-holder upper plate 42. The probe-holder upper plate 42 and the probe-holder lower plate 44 are spaced from each other in a vertical direction by inner spacers 46a and 46b.

Attached to the ends of the probe-holder upper plate 42 are outer spacers 48a and 48b that are located outward from the inner spacers 46a and 46b and hang downward from the probe-holder upper plate 42 so that they are horizontally aligned with the inner spacers 46a and 46b.

The inner and upper spacers 446a, 46b and 48a, 48b, respectively, are interconnected by leaf springs 50a, 50b, 50c, 50d, 50e, 50f, 50g, and 50h, respectively (FIG. 3). In such a construction, the probe-holder upper plate 42 is stationary, while the probe-holder lower plate 44 that rigidly holds the test probe 29 is resiliently secured relative to the probe-holder upper plate 42 and may perform resilient vertical movement in the direction of the Z-axis together with the test probe 29 attached to this plate.

As can be seen from the exploded view of FIG. 4, the sensor-holding sub-unit 38 contains an upper sensor-holding plate 38a and a lower sensor-holding plate 38b. Each sensor-holding plate has rigid blocks at two diametrically opposite corners firmly attached to the respective sensor-holding plates. Thus, the upper sensor-holding plate 38a has a rigid block 38a1 (shown by broken lines in FIG. 4) and a diametrically opposite rigid block 38a2. On the other hand, the lower sensor-holding plate 38b has a rigid block 38b1 and a diametrically opposite rigid block 38b2. Attached to the inward facing surface of the block 38a1 is a flexible beam 38c1 that in the illustrated embodiment extends parallel to the side 38a' of the plate 38a, i.e., to the axis X (see FIG. 1). Similarly, attached to the inward facing surface of the block 38b1 is a flexible beam 38c2 that in the illustrated embodiment extends parallel to the side 38b' of the plate 38b, i.e., to the axis X (see FIG. 1).

In an assembled state of the sensor-holding sub-unit 38 shown in FIG. 2, the flexible beam 38c1 is spaced from the surface of the upper sensor-holding plate 38a with the gap G1 (FIG. 2), and flexible beam 38c2 is spaced from the surface of the lower sensor-holding plate 38b with the gap G2, which is equal to the gap G1. In fact, both flexible beams are spaced from both upper and lower plates so that the plates and beam together form a flexible parallelogram with the upper plate 38a and the lower plate 38b flexibly moveable coplanar to each other when the flexible beams 38c1 and 38c2 are resiliently deformed.

In other words, the rigid blocks 38a1, 38a2, 38b1, and 38b2 function as spacers that space the upper sensor-holding plate 38a and the lower sensor-holding plate 38b parallel to each other and at a certain distance from each other, while the flexible beams 38c1 and 38c2 function like elastic or flexible members that allow the plates to shift coplanar to each other in the horizontal plane under the effect of a friction force F (see FIG. 1) that is developed during reciprocations of the test specimen 34 relative to the test probe 29, in the illustrated case, in the direction of the axis X, or under effect of a tangentially directed friction force (not shown) when the test specimen 34 performs rotary motion relative to the test probe 29.

It also should be noted that the rigid blocks 38a1, 38a2, 38b1, and 38b2 and the respective flexible beams of the upper and lower sensor-holding plates 38a and 38b have an oppositely symmetric arrangement.

As shown in FIGS. 5(a) and 5(b), in the illustrated embodiment, the upper and lower sensor-holding plates 38a and 38b have freedom of movements only in X-axis direction and are restrained from the movements in the Y-axis direction. FIG. 5(a) shows positions of the plates 38a and 38b and the deformed flexible beams C1 and C2 (drawn by broken lines) when the plates are shifted in one direction, and FIG. 5(b) shows positions of the plates 38a and 38b and the deformed flexible beams C1 and C2 (drawn by broken lines) when the plates are shifted in the opposite direction.

Mobility of the sensor unit 22 in the Z-axis direction relative to the attachment unit 30 is provided by leaf springs 50a, 50b, 50c, 50d, 50e, 50f, 50g, and 50h, shown in FIG. 3, and the deformation pattern in the Z-axis direction is shown in FIGS. 6(a) and 6(b). These drawings show two different positions of the test probe 29 relative to the specimen 34. The force F, shown in FIG. 6(b) designates not only the vertical loading force but also the force used for determining hardness of the material in case hardness measurement when the driven in the direction of X or Y axis is stopped and the moveable stage 32 (FIG. 1) with the test specimen is moveable against the test probe that holds an appropriate hardness-testing tip 29-2. In the hardness test the leaf springs 50a, 50b, 50c, 50d, 50e, 50f, 50g, and 50h provide smooth gradual development of the force applied to the specimen. This feature contributes to better accuracy of measurement.

In FIG. 2 reference numerals 52a, 52b, 52c, and 52d designate pressure sensitive members which are deformed under the effect of a compression force and which support respective pressure sensors 52a-1, 52b-1, and two other similar sensors which cannot be seen since they are located on the rear sides of the pressure sensitive members 52c, and 52d. In hardness test the data from the pressure sensors are used for determination of hardness.

Thus, the adapter plate 40, the upper sensor-holding plates 38a, and pressure sensitive members 52a, 52b, 52c, and 52d form a pressure-sensor holding unit 53.

When the sensor unit 22 moves in the Z-axis direction relative to the attachment unit 30, as shown in FIGS. 6(a) and 6(b), the aforementioned sensors 52a-1, 52b-1, etc. of the pressure-sensor holding unit measure a force acting in the Z-axis direction. Such pressure sensors can be represented by tension sensors, film piezo sensors, or the like and can be pasted to the deformable surfaces in a manner known in the art. The number and arrangement of the sensors may vary but for convenience of operation and calibration it is recommended that the of the sensors on the pressure sensitive members 52a, 52b, and 52c, 52d be arranged symmetrically opposite to each other.

In the illustrated embodiment, the sensor unit 22 has a structure which is deformable under the effect of the friction force between the specimen 34 and the tip of the probe 29 only in one horizontal direction, e.g., in the X-axis direction and is resistance to deformations in the Y-axis direction. In fact, the principle of the invention allows to measure the forces in both X and Y-axes directions by providing the sensor unit 22 with another pair of the upper and lower sensor-holding plates but with arrangement of flexible beams shifted 90° relative to the flexible beams 38c1 and 38c2 (FIG. 4).

Referring back to FIG. 4, it can be seen that the flexible beam 38c1 supports a sensor 38c1-1, and the flexible beam 38c2 supports a sensor 38c2-1. When during the test a horizontal friction force F is developed in the X-axis direction between the specimen 34 and the tip of the probe 29 (FIG. 1), this force deforms the flexile beams 38c1 and 38c2 as shown in FIG. 5(a) and FIG. 5(b) and thus activates the sensors 38c1-1 and 38c2-1 (FIG. 4).

Similar to the pressure sensors of FIG. 2, the sensors 38c1-1 and 38c2-1 can be represented by tension sensors, film piezo sensors, or the like and can be pasted to the deformable surfaces by a manner known in the art. The number and arrangement of the sensors may vary but for convenience of operation and calibration it is recommended that the sensors on the flexible beams 38c1 and 38c2 be arranged symmetrically opposite to each other.

It should be understood that the term "flexible" is applied to the beams 38c1 and 38c2 just to show that these beams possess a certain flexibility in the X-axis direction but the magnitude of bending deformation is extremely small in comparison to the cross-sectional area of the beam.

The sensors may be combined into two-dimensional load cells. One such cell (not shown) may contain two or four strain gauges for X-axis measurements and one such cell may contain two or four strain gauges for Z-axis measurements. The strain gauge signals may be converted to voltages by respective amplifiers (not shown) to provide X and a Z load signals. The signals are shown in the screen of a display as bar graphs or similar.

Thus, it has been shown that the structure of the sensor unit 22 and the geometry of its parts proposed by the present invention make it possible to completely isolate deformations of the parts in the Z-axis direction from the deformations of the parts in the X-axis direction. As a result, it is possible to exclude cross-talks between the sensors acting in the Z-axis direction and the sensors acting in the X-axis direction.

Figure 7:
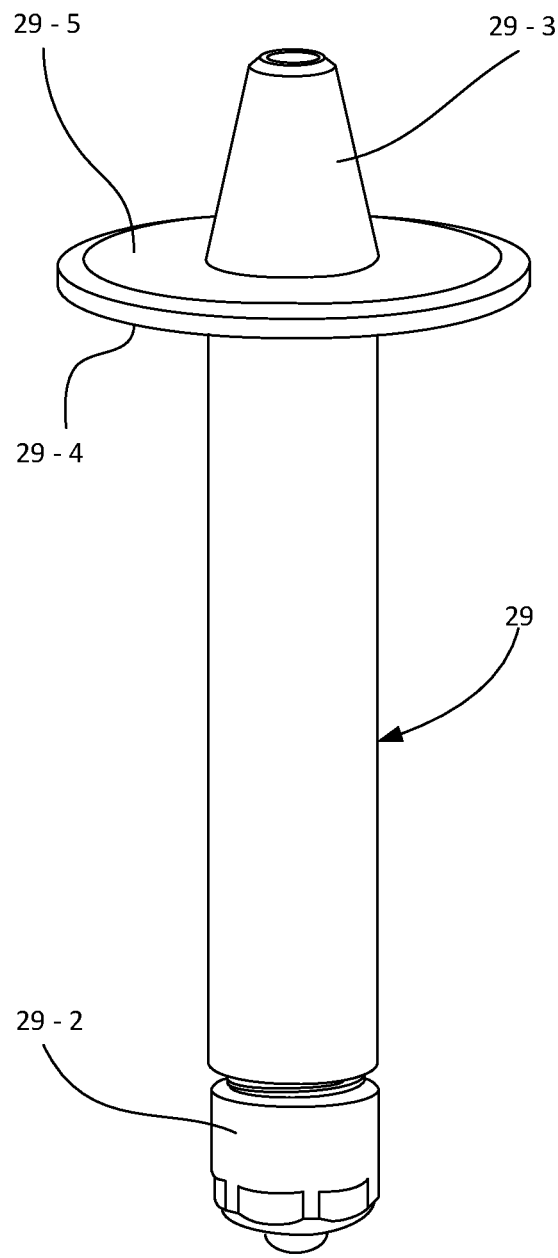
FIG. 7 is a three-dimensional view of the test probe for the tester of the invention.
Figure 8:
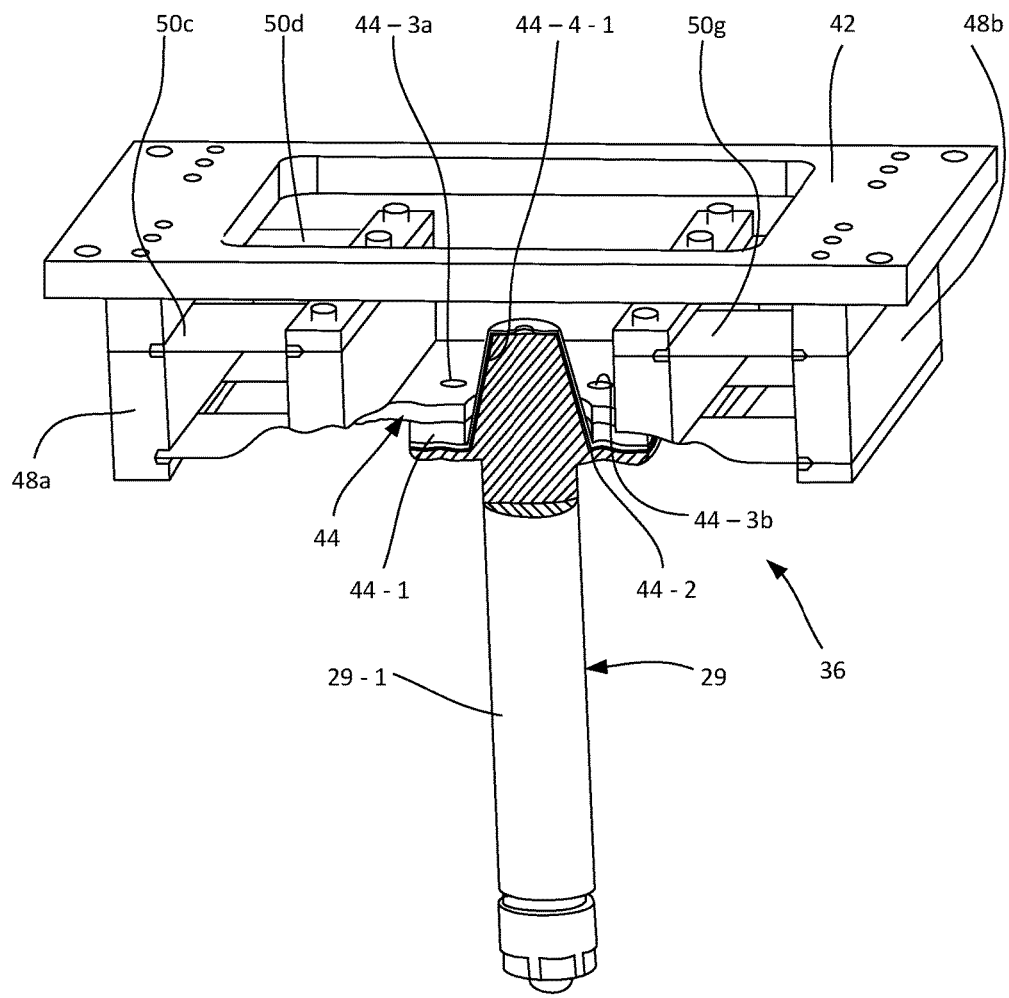
FIG. 8 is a view similar to FIG. 3 but illustrating the probe quick-release means of the resilient probe holder.

In addition to the characteristics described above, the structure of the resilient probe holder 36 imparts to the probe soft-touch and quick-release features. This is shown in FIGS. 7 and 8, wherein FIG. 7 is a three-dimensional view of the test probe 29, and FIG. 8 is a view similar to FIG. 3 but illustrating the probe quick-release means of the resilient probe holder 36.

More specifically, the probe 29 has a shaft portion 29-1 with a replaceable tip portion 29-2 on one end and a tapered tail portion 29-3 with a flange 29-4 between the tail portion 29-3 and the shaft portion 29-1. The tail-facing side of the flange is coated with a layer 29-5 of a magnetic or easily magnetized material (hereinafter referred to as a "magnetized material layer"). The replaceable tip 29-2 may be provided with a hardness-measuring ball for measuring Brinell hardness, with a diamond pin for measuring Rockwell hardness, or the like.

On the other hand, a magnet 44-1 with a central opening 44-2 is attached to the lower side of the lower plate 44, e.g., by screws 44-3a, 44-3b, and a hollow tapered probe tail receiver 44-4 made from a magnetic or magnetized material is inserted through the aforementioned opening 44-2 so that the tapered portion protrudes upward from the surface of the lower plate 44. At its lower end, the hollow tapered probe tail receiver 44-4 has a flange for attachment of the hollow probe tail receiver 44-4 to the magnet 44-1.

The cavity 44-4-1 of the probe tail receiver 44-4 has the same taper angle as the tail portion 29-3 of the probe and is intended for receiving the latter.

The magnet 44-1 develops a sufficient magnetic attraction force to firmly hold the flange portion 29-5 of the probe but at the same time to allow easy manual retraction, i.e., quick disconnection of the probe from the resilient probe holder 36.

The provision of leaf springs 50a, 50b, 50c, 50d, 50e, 50f, 50g, and 50h (FIG. 3) imparts elastic mobility to the resilient probe holder 29 and thus a soft touch at contact of the tip of the probe 29-2 with the test specimen.

The invention has been described in detail with reference to specific examples and illustrated with reference to specific drawings. It should be noted, however, that these descriptions and drawings should not be construed as limiting the application of the invention and that any changes and modifications are possible within the scope of the attached patent claims. For example, sensors of types other than those described can be used and their arrangement also can be changed. The specimen can be driven in the Y-axis direction and in that case the friction force will be measured in the Y-axis directions. Alternatively, the structure may be two-layered with two sensor units shifted 90° with respect to each other.

What is claimed is:

1. A universal material tester with quick-release test probe and reduced cross-talk between the sensors comprising:
   a rigid housing supporting a sensor unit and a test probe rigidly secured in the sensor unit and extending in the vertical direction;
   a table supported by the rigid housing which supports a test specimen and is moveable in a vertical direction toward and away from the test probe and at least in one horizontal direction for providing friction contact between the test probe and the test specimen, wherein the sensor unit comprises:
   a pressure-sensor holding unit provided with pressure sensors for measuring a pressure force applied from the test specimen to the test probe in the vertical direction;
   a resilient probe holder that holds the test probe; and
   a horizontal-axis sensor-holding sub-unit installed between the pressure-sensor holding unit and the resilient probe holder;
   the resilient probe holder having a first resilient means that resiliently supports the test probe relative to the sensor unit and allows the test probe to resiliently move in the vertical direction but does not allow the resilient probe to move in the horizontal direction; and
   the horizontal-axis sensor-holding sub-unit having second resilient means that resiliently supports the resilient probe holder relative to the sensor unit to allow the resilient probe holder with the test probe to resiliently move at least in one horizontal direction.

2. The tester according to claim 1, wherein the horizontal-axis sensor-holding sub-unit comprises an upper sensor-holding plate and a lower sensor-holding plate interconnected through the second resilient means.

3. The tester according to claim 2, wherein the second resilient means comprises: a first rigid block secured to the upper sensor-holding plate and a first flexible elongated beam one end of which is attached to the first rigid block and which is installed with a gap relative to the upper sensor-holding plate; and a second rigid block secured to the lower sensor-holding plate and a second flexible elongated beam one end of which is attached to the second rigid block and which is installed with a gap relative to the lower sensor-holding plate, the other end of the first flexible elongated beam being attached to the second rigid block, and the other end of the second flexible elongated beam being attached to the first rigid block.

4. The tester according to claim 3, wherein the rigid blocks and the flexible elongated beams associated with the upper sensor-holding plate and the lower sensor-holding plate have a symmetrically opposite arrangement.

5. The tester according to claim 4, further comprising horizontal force measurement sensors for measuring a friction force applied to the test probe during the test, the horizontal force measurement sensors being pasted to the first and second flexible elongated beams.

6. The tester according to claim 3, further comprising horizontal force measurement sensors for measuring a friction force applied to the test probe from the test specimen during the test, the horizontal force measurement sensors being pasted to the first and second flexible elongated beams.

7. The tester according to claim 1, wherein the resilient probe holder comprises a probe-holder upper plate and a probe holder lower plate, which are spaced from each other, wherein the probe-holder upper plate is rigidly connected to the horizontal-axis sensor-holding sub-unit, and the probe-holder lower plate is resiliently connected to the probe-holder upper plate by said first resilient means.

8. The tester according to claim 7, wherein the test probe has a tapered tail portion on one end that faces the pressure-sensor holding unit and probe-holder lower plate has a tapered probe tail receiver provided with a probe quick-release means for quick-release of the test probe from the probe-holder.

9. The tester according to claim 8, wherein the probe quick-release means comprises a magnet.

10. A universal wear and friction tester with reduced cross-talk between the sensors comprising:
    a rigid housing supporting a sensor unit and a test probe rigidly secured in the sensor unit and extending in the vertical direction;
    a table supported by the rigid housing which supports a test specimen and is moveable in a vertical direction toward and away from the test probe and at least in one horizontal direction for providing friction contact between the test probe and the test specimen, wherein the sensor unit comprises:
    a pressure-sensor holding unit provided with pressure sensors for measuring a pressure force applied from the test specimen to the test probe in the vertical direction;
    a resilient probe holder that holds the test probe; and
    a horizontal-axis sensor-holding sub-unit comprising a flexible parallelogram installed between the pressure-sensor holding unit and the resilient probe holder;
    the resilient probe holder having first resilient means that resiliently supports the test probe relative to the sensor unit and allows the test probe to resiliently move in the vertical direction but does not allow the resilient probe to move in the horizontal direction;
    the horizontal-axis sensor-holding sub-unit having second resilient means that resiliently supports the resilient probe holder relative to the sensor unit to allow the resilient probe holder with the test probe to resiliently move at least in one horizontal direction.

11. The tester according to claim 10, wherein the resilient parallelogram comprises: an upper sensor-holding plate, the lower sensor-holding plate, and a second resilient means that interconnects the upper sensor-holding plate, the lower sensor-holding plate.

12. The tester according to claim 11, wherein the second resilient means comprises: a first rigid block secured to the upper sensor-holding plate and a first flexible elongated beam one end of which is attached to the first rigid block and which is installed with a gap relative to the upper sensor-holding plate; and a second rigid block secured to the lower sensor-holding plate and a second flexible elongated beam one end of which is attached to the second rigid block and which is installed with a gap relative to the lower sensor-holding plate, the other end of first flexible elongated beam being attached to the second rigid block, and the other end of the second flexible elongated beam being attached to the first rigid block.

13. The tester according to claim 12, wherein the rigid blocks and the flexible elongated beams associated with the upper sensor-holding plate and the lower sensor-holding plate have a symmetrically opposite arrangement.

14. The tester according to claim 13, further comprising horizontal force measurement sensors for measuring a friction force applied to the test probe from the test specimen during the test, the horizontal force measurement sensors being pasted to the first and second flexible elongated beams.

15. The tester according to claim 10, wherein the resilient probe holder comprises a probe-holder upper plate and a probe holder lower plate, which are spaced from each other, wherein the probe-holder upper plate is rigidly connected to the horizontal-axis sensor-holding sub-unit, and the probe-holder lower plate is resiliently connected to the probe-holder upper plate by said first resilient means.

16. The tester according to claim 15, wherein the test probe has a tapered tail portion on one end that faces the pressure-sensor holding unit and probe-holder lower plate has a tapered probe tail receiver provided with a probe quick-release means for quick-release of the test probe from the probe-holder.

17. The tester according to claim 16, wherein the probe quick-release means comprises a magnet.

* * * * *